US00PP23352P2

(12) United States Plant Patent
Hofmann

(10) Patent No.: US PP23,352 P2
(45) Date of Patent: Jan. 22, 2013

(54) ***NEMESIA* PLANT NAMED 'NESPLUGOYEL'**

(50) Latin Name: *Nemesia hybrida*
Varietal Denomination: Nesplugoyel

(75) Inventor: Silvia Hofmann, Mainz (DE)

(73) Assignee: InnovaPlant GmbH & Co., KG, Gensingen (DE)

( * ) Notice: Subject to any disclaimer, the term of this patent is extended or adjusted under 35 U.S.C. 154(b) by 77 days.

(21) Appl. No.: 12/927,998

(22) Filed: Dec. 1, 2010

(51) Int. Cl.
*A01H 5/00* (2006.01)

(52) U.S. Cl. ..... Plt./458

(58) Field of Classification Search ..... Plt./458
See application file for complete search history.

*Primary Examiner* — June Hwu
(74) *Attorney, Agent, or Firm* — Mark P. Bourgeois

(57) ABSTRACT

A new cultivar of *Nemesia* plant named 'Nesplugoyel' that is characterized by good high temperature tolerance, profuse golden yellow flowers and a semi-trailing habit.

1 Drawing Sheet

Botanical classification: *Nemesia hybrida.*
Variety denomination: 'Nesplugoyel'.

BACKGROUND OF THE INVENTION

The present invention relates to a new and distinct cultivar of *Nemesia* plant botanically known as *Nemesia hybrida* and hereinafter referred to by the cultivar name 'Nesplugoyel'.

The new *Nemesia* is the product of a planned breeding program conducted by the inventor in Gensingen, Germany. The objective of the breeding program is to create new *Nemesia* cultivars with unique flower colors and improved high temperature tolerance.

'Nesplugoyel' is a hybrid that originated from a crossing in the Summer of 2003 of the female or seed parent a proprietary *Nemesia* identified as Neb Goldgelb VI (not patented) and the male or pollen parent a proprietary *Nemesia* identified as White Dream I tet 7 (not patented). The resulting seeds were subsequently planted and grown. The cultivar 'Nesplugoyel' was selected by the inventor in the Spring of 2004 as a single plant within the progeny of the stated cross in Gensingen, Germany.

Asexual reproduction of the new cultivar 'Nesplugoyel' first occurred by terminal cuttings in July of 2004 in Gensingen, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Nemesia* cultivar 'Nesplugoyel'. These traits in combination distinguish 'Nesplugoyel' as a new and distinct cultivar apart from other existing known varieties of *Nemesia.*

1. *Nemesia* 'Nesplugoyel' exhibits good high temperature tolerance.
2. *Nemesia* 'Nesplugoyel' exhibits golden yellow flowers.
3. *Nemesia* 'Nesplugoyel' exhibits profuse continuous flowering.
4. *Nemesia* 'Nesplugoyel' exhibits a semi-trailing habit.

The closest comparison cultivars are *Nemesia* 'Innsuncara' (U.S. Plant Pat. No. 21,096) and *Nemesia* 'Inntraibana' (not patented).

'Nesplugoyel' is distinguishable from *Nemesia* 'Innsuncara' by the following characteristics:

1. 'Nesplugoyel' has a larger number of flowers.
2. 'Nesplugoyel' has smaller flowers than 'Innsuncara'.
3. 'Nesplugoyel' exhibits a more trailing habit.
4. 'Nesplugoyel' has better high temperature tolerance than 'Innsuncara'.

'Nesplugoyel' is distinguishable from 'Inntraibana' by the following characteristics:

1. 'Nesplugoyel' exhibits a less trailing habit.
2. 'Nesplugoyel' has smaller flowers than 'Inntraibana'.
3. 'Nesplugoyel' has darker yellow flowers than 'Inntraibana'.
4. 'Nesplugoyel' has better high temperature tolerance than 'Inntraibana'.

'Nesplugoyel' is distinguishable from the female or seed parent *Nemesia* Neb Goldgelb VI by the following characteristics:

1. 'Nesplugoyel' has smaller flowers.
2. 'Nesplugoyel' has smaller leaves.
3. 'Nesplugoyel' has a semi-trailing habit. Neb Goldgelb VI has an upright habit.
4. 'Nesplugoyel' has better high temperature tolerance.

'Nesplugoyel' is distinguishable from the male or pollen parent *Nemesia* White Dream I tet 7 by the following characteristics:

1. 'Nesplugoyel' has yellow flowers. The flowers of White Dream I tet 7 are white.
2. 'Nesplugoyel' exhibits a larger number of branches.
3. 'Nesplugoyel' exhibits more vigorous growth.

BRIEF DESCRIPTION OF THE DRAWING

The accompanying photograph illustrates the distinguishing traits of *Nemesia* 'Nesplugoyel'. The plant in the photograph shows an overall view of a 20 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Nemesia* cultivar named 'Nesplugoyel'. Data was collected in Gensingen, Germany from 20 week old glass greenhouse grown plants in 12 cm. diameter containers. The time of year was Summer and the temperature range was 16-35 degrees Centigrade during the day and 12-16 degrees Centigrade at night. The light level was natural light. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Nesplugoyel' has not been tested under all possible conditions and phenotypic differences may be observed with variations in environmental, climatic, and cultural conditions, however, without any variance in genotype.

Botanical classification: *Nemesia hybrida* 'Nesplugoyel'.
Annual or perennial: Annual.
Parentage: 'Nesplugoyel' is the product of the female or seed parent *Nemesia* Neb Goldgelb VI and the male or pollen parent *Nemesia* White Dream I tet 7.
Vigor: Strong.
Growth habit: Semi-trailing/prostrate.
Plant shape: Spreading, bushy.
Suitable container size: 12 cm. pots.
Height: 20 cm. in height.
Width: 15 cm. in width.
Low temperature tolerance: 0° Centigrade.
High temperature tolerance: 40° Centigrade.
Propagation: Terminal cuttings.
Time to initiate roots in summer: 10 to 12 days to initiate roots at 18 to 20° Centigrade.
Time to initiate roots in winter: 14 to 16 days to initiate roots at 16° Centigrade.
Time to produce a rooted cutting or liner in summer: 10 to 12 days at 16 to 18° Centigrade.
Time to produce a rooted cutting or liner in winter: 18 to 20 days at 16° Centigrade.
Crop time: Approximately 6 to 8 weeks.
Root system: Fine and fibrous.
Stem:
- *Branching habit*.—Lateral branches grow from every non-flowering axil.
- *Basal branching*.—Yes.
- *Average number of lateral branches*.—5.
- *Pinching*.—Yes.
- *Lateral branch dimensions*.—7 mm. in diameter and 8 to 12 cm. in length.
- *Internode length*.—15 to 22 mm.
- *Stem shape*.—Square with ridges at the corners.
- *Stem strength*.—Very strong.
- *Stem color*.—138C.
- *Pubescence*.—Absent.

Foliage:
- *Leaf arrangement*.—Opposite.
- *Compound or single*.—Single.
- *Number of leaves per lateral branch*.—6.
- *Leaf shape*.—Lanceolate.
- *Leaf apex*.—Acuminate.
- *Leaf base*.—Attenuate.
- *Leaf dimensions*.—20 cm. in length and 7 cm. in width.
- *Texture*.—Glabrous on both surfaces.
- *Pubescence*.—None.
- *Leaf margin*.—Serrated.
- *Venation pattern*.—Simple.
- *Young leaf color* (*upper surface*).—N137B.
- *Young leaf color* (*lower surface*).—138D.
- *Mature leaf color* (*upper surface*).—N137A.
- *Mature leaf color* (*lower surface*).—137C.
- *Vein color* (*upper surface*).—137B.
- *Vein color* (*under surface*).—137D.
- *Leaf attachment*.—Sessile.
- *Durability of foliage to stress*.—High.

Flower:
- *Inflorescence arrangement*.—Raceme.
- *Inflorescence dimensions*.—15 cm. in height and 2 cm. in width.
- *Quantity of flowers per inflorescence*.—3 to 5.
- *Flower type*.—Zygomorphic.
- *Flowering habit*.—Apical in succession.
- *Quantity of flowers per lateral stem*.—3 to 5.
- *Quantity of flower buds per lateral stem*.—3.
- *Quantity of flowers and buds per plant*.—Average 150.
- *Natural flowering season*.—April to October.
- *Time to flower*.—5 weeks.
- *Rate of flower opening*.—Every 4 to 6 days.
- *Fragrance*.—Slight.
- *Flower bud length*.—5 mm.
- *Flower bud diameter*.—2.5 mm. in diameter.
- *Flower bud shape*.—Ovate.
- *Bud color*.—1D.
- *Rate of bud opening*.—3 days.
- *Flower aspect*.—Outward/upright.
- *Flower shape*.—Zygomorphic.
- *Flower dimensions*.—17 to 22 mm. in diameter and 20 to 22 mm. in height.
- *Flower longevity*.—3-5 days.
- *Number of petals*.—5.
- *Fused or unfused*.—Fused.
- *Petal arrangement*.—4 upper petal lobes and two lower petal lobes fused into a lip.
- *Upper petal lobes shape*.—Rounded.
- *Lower petal lobes shape*.—Spathulate.
- *Petal texture*.—Smooth on both surfaces (upper and lower lobes).
- *Upper petal lobes margin*.—Rounded.
- *Lower petal lobes margin*.—Slightly undulate.
- *Petal apex*.—Obtuse (upper and lower lobes).
- *Petal base*.—Fused (upper and lower lobes).
- *Upper petal lobes dimensions*.—18 mm. in width and 10 mm. in length.
- *Lower petal lobes dimensions*.—15 mm. in width and 8 mm. in length.
- *Petal color when opening* (*upper side, upper and lower lobes*).—3A.
- *Petal color when opening* (*under side, upper and lower lobes*).—8D.
- *Petal color fully opened* (*upper side, upper and lower lobes*).—3B.
- *Petal color fully opened* (*under side, upper and lower lobes*).—8D.
- *Palate color* (*lower petal*).—14B.
- *Basal blotch color* (*upper petal lobe*).—5C.
- *Petal vein color* (*upper petal lobe*).—N89B.
- *Petal color fading to* (*upper and lower lobes*).—1D.

*Palate pubescence*.—Covered with short dense hairs.
*Nectar spur dimensions.*—5 mm. in length and 1.5 mm. in width.
*Nectar spur color.*—6B.
*Self-cleaning or persistent*.—Self-cleaning.

Sepals:
*Sepal arrangement*.—Fused to calyx.
*Number of sepals.*—5.
*Sepal shape*.—Lanceolate.
*Sepal margin*.—Pubescent.
*Sepal apex*.—Acuminate.
*Sepal base*.—Fused.
*Sepal dimensions.*—3 mm. in length and 1 mm. in width.
*Young sepal color* (*upper side*).—136B.
*Young sepal color* (*under side*).—136B.
*Mature sepal color* (*upper side*).—136B.
*Mature sepal color* (*under side*).—136B.

Calyx:
*Calyx shape*.—Lyriform.
*Calyx dimensions.*—4 mm. in length and 2 mm. in diameter.

Pedicel:
*Pedicel length.*—15 mm.
*Pedicel texture*.—Pubescent.
*Pedicel color.*—138B.

Peduncle:
*Peduncle dimensions.*—20 mm. in length and 1 mm. in diameter.
*Peduncle angle.*—30 degrees from stem.
*Peduncle strength*.—Moderate.
*Peduncle color.*—136B.

Reproduction organs:
*Stamen number.*—5.
*Anther shape*.—Oval.
*Anther size.*—0.5 mm.
*Anther color.*—4B.
*Amount of pollen*.—Low.
*Pollen color.*—4B.
*Pistil number.*—1.
*Pistil length.*—1.5 mm.
*Stigma shape*.—Dentate.
*Stigma color.*—140C.
*Style length.*—1 mm.
*Style color.*—104C.
*Ovary color.*—104C.

Fruit: None, sterile triploid.

Disease and pest resistance: Disease and pest resistance has not been observed.

The invention claimed is:

1. A new and distinct variety of *Nemesia* plant named 'Nesplugoyel' as described and illustrated.

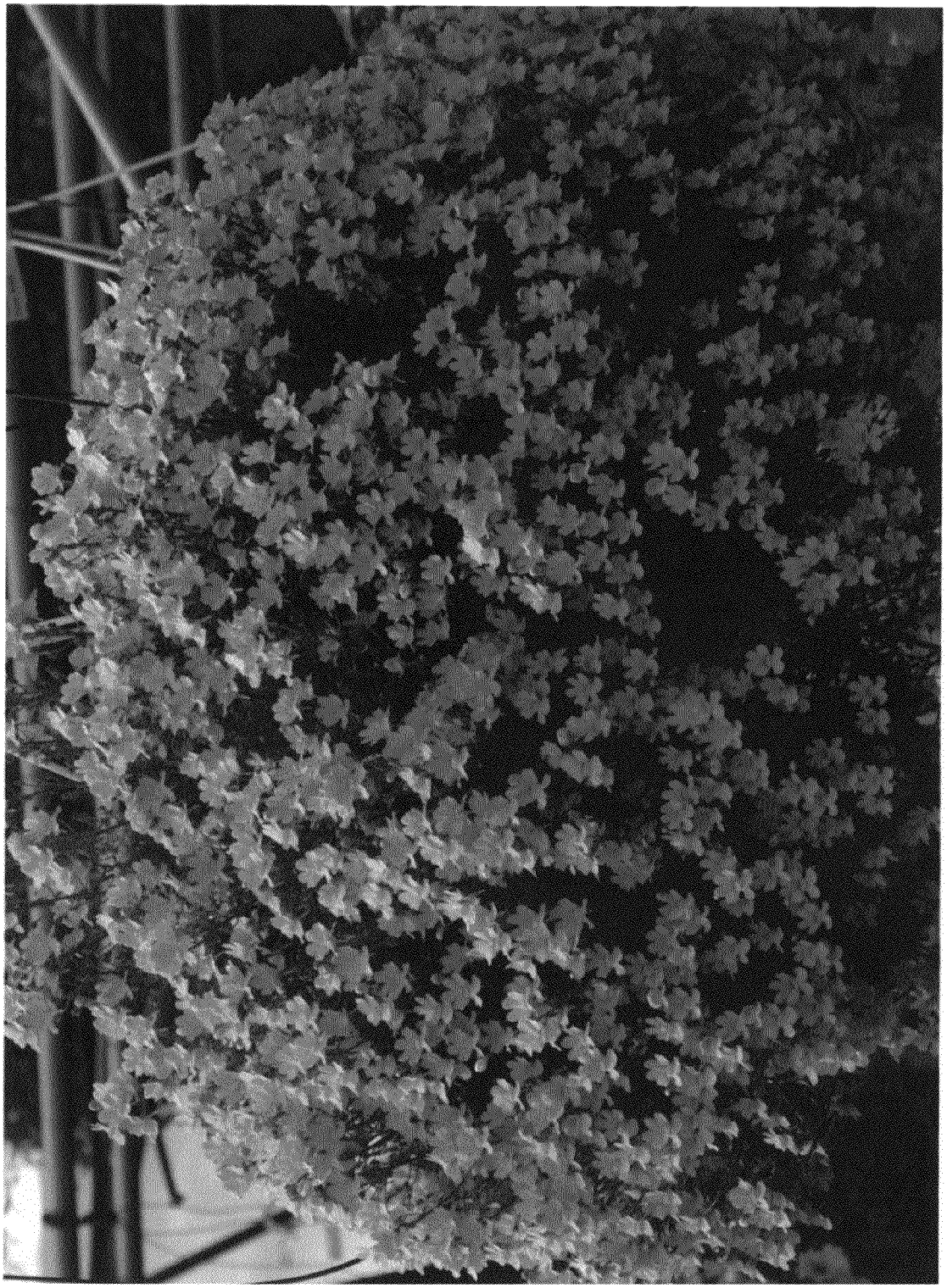

* * * * *